United States Patent [19]
Swette et al.

[11] Patent Number: 5,964,992
[45] Date of Patent: Oct. 12, 1999

[54] REFERENCE ELECTRODE FOR MONITORING STEEL-IN-CONCRETE POTENTIALS

[75] Inventors: Larry L. Swette, Newton; Mourad Manoukian, Waltham; Monjid Hamdan, Worcester; Anthony LaConti, Lynnfield, all of Mass.; Ali Akbar Sohanghpurwala, Sterling; William T. Scannell, Purcellville, both of Va.

[73] Assignee: Giner, Inc., Waltham, Mass.

[21] Appl. No.: 09/119,224

[22] Filed: Jul. 20, 1998

[51] Int. Cl.[6] ........................................ C25B 11/00
[52] U.S. Cl. .................. 204/290 R; 204/294; 204/435; 204/404; 204/196.06; 204/196.38
[58] Field of Search ...................................... 204/196, 404, 204/290 R, 291, 435, 294; 205/734, 739

[56] References Cited

U.S. PATENT DOCUMENTS

| | | | |
|---|---|---|---|
| 4,255,241 | 3/1981 | Kroon et al. | 204/147 |
| 4,474,606 | 10/1984 | McKaveney et al. | 106/1.17 |
| 4,861,453 | 8/1989 | Matsouka et al. | 204/404 |
| 4,892,637 | 1/1990 | Sauer et al. | 204/294 |
| 5,015,355 | 5/1991 | Schiessl et al. | 204/404 |
| 5,259,944 | 11/1993 | Feliu et al. | 204/404 |
| 5,314,599 | 5/1994 | Allaire | 204/294 |
| 5,403,550 | 4/1995 | Bernhard | 422/53 |
| 5,677,367 | 10/1997 | Savin | 523/219 |

*Primary Examiner*—Bruce F. Bell

[57] ABSTRACT

A graphite reference electrode for use in the cathodic protection of steel embedded in concrete has been produced with a stable catalyzed structure that when equilibrated with air or oxygen and an electrolyte reaches a reproducible and reversible redox potential. This stable device is produced by exposure to hydrogen peroxide, impregnating with a metal oxide followed by a coating treatment. The embedded catalyzed graphite reference electrodes can be used in impressed cathodic protection systems or monitoring the corrosion condition of embedded steel to provide an early warning of impending damage.

8 Claims, No Drawings

REFERENCE ELECTRODE FOR MONITORING STEEL-IN-CONCRETE POTENTIALS

BACKGROUND OF THE INVENTION

Corrosion of steel in concrete, especially reinforcement bars in concrete, has evolved over the past two decades to become the single most costly problem of its type in the U.S. Cost estimates for repairing the present damage on the highway bridges approach 20 billion dollars according to the Transportation Research Board. Cathodic protection systems are presently being used to mitigate corrosion in conventionally reinforced concrete members, and their use is being contemplated on prestressed bridge components. The use of embedded reference electrodes or reference cells in conjunction with cathodic protection of conventionally reinforced concrete bridge members is desirable, and is essential for application of cathodic protection to prestressed concrete bridge components.

For cathodic protection systems to be successful in mitigating corrosion without causing hydrogen embrittlement of the embedded steel reinforcement bars, the amount of polarization of the embedded steel must be very accurately controlled. To monitor accurately and to control the amount of polarization of prestressing steel, stable and reliable embedded reference electrodes are needed. Such reference electrodes can also prove useful during cathodic protection of conventionally reinforced bridge components to provide a means for cost-effective monitoring and to avoid overprotection.

Several different types of reference cells have been used in field trials and in full scale cathodic protection systems. Their field performance history along with the results of laboratory studies have indicated potential problems of long term stability and reliability. Although portable copper-copper sulfate (Cu—$CuSO_4$) reference cells are widely used for surface potential surveys in which their performance has been satisfactory, the use of embedded Cu—Cu—$SO_4$ reference cells has been restricted due to leakage, drying out and/or freezing of the electrolyte in the cell. Also, copper sulfate leaking from a cell can react with water in pores in the concrete and generate undesirable products.

The most widely used embedded reference cells in cathodic protection work are silver-silver chloride (Ag—AgCl), but due to the instability of these cells they are most often used only for short term monitoring of potentials rather than for cathodic protection systems. Their low temperature response is very erratic, and they are also sensitive to the chloride content of the concrete. Another drawback of these reference cells is that they develop a variable and high resistance. We have found the resistance between the Ag—AgCl cell and the reinforcement bar to vary from a few hundred to a few hundred thousand ohms for cells embedded in similar concrete in the same bridge deck and at the same temperature.

Zinc-zinc sulfate (Zn—$ZnSO_4$) cells have been used extensively, but the stability of these cells is a problem. They are found to be sufficiently stable to conduct short-term monitoring and performed well in laboratory studies, but many of the Zn-$ZnSO_4$ cells become unstable after one year of outdoor exposure and as a consequence, potential measurements can fluctuate widely. Zn—$ZnSO_4$ cells are also strongly affected by low temperatures.

We have found the performance and stability of graphite that is used as a reference electrode can be significantly improved by selective treatment to improve exchange current densities when in equilibrium with air or oxygen and decrease peroxide accumulation. The forming of a stable carbon reference electrode by 1) hydrogen peroxide ($H_2O_2$) chemical pre-treatment, 2) doping with manganese dioxide ($MnO_2$), and 3) subsequent wetproofing with a thin porous fluorocarbon layer combined with a conductive ceramic outer layer has been discovered to give enhanced carbon reference electrode stability.

Kroon et al., in patent U.S. Pat. No. 4,255,241 entitled "Cathodic protection apparatus and method for steel reinforced concrete structures," describe a system comprising anodes encased in a carbonaceous material matrix and placed within slots cut in a concrete structure. A current for cathodic protection is applied between the anodes and the steel in the concrete structure. Matsuoka et al., in patent U.S. Pat. No. 4,861,453 entitled "Corrosion detecting probe for steel buried in concrete," describe a probe comprising of an electrode assembly placed within a container filled with an electrolyte solution. The container, made of an electrically insulating material includes an open end which is placed in close contact with a concrete surface under which is buried steel members. Said electrode assembly is attached via terminals to a electrochemical measuring apparatus for evaluating the corrosive state of the underlying steel members. Schiessi, in patent U.S. Pat. No. 5,015,355 entitled "Corrosion measuring cell," describes a cell comprising a corrosion-resistant cathode electrode and ordinary steel anodes which are separated and embedded in a concrete section for which the degree of corrosion in the underlying steel reinforcement members is desired. The cathode and anodes are electrically connected via a current measuring device. Feliu et al., in patent U.S. Pat. No. 5,259,944 entitled "Corrosion detecting probes for use with a corrosion-rate meter for electrochemically determining the corrosion rate of reinforced concrete structures," describe a probe comprising an electrode assembly which is positioned on a concrete surface containing metallic members. A corrosion-rate meter is coupled to the electrode assembly as well as the metal reinforcement members and wet spongy material is used electrolytic conduction. Bernhard, in patent U.S. Pat. No. 5,403,550 entitled "Electrode for determining the state of corrosion of metal reinforcement in concrete constructions," present an electrode comprising an insulated wire made of metal more electrochemically positive than the metal reinforcement members. This wire is embedded in the concrete and placed in electrolytic contact with the metal reinforcement members via moisture in the concrete. The insulation of the wire is either plastic or a material with equivalent electrical properties to that of concrete. A separate apparatus is used to measure the potential between the wire electrode and the metal reinforcement members.

None of the inventions described in these patents disclose a multilayer reference electrode having high stability for oxygen reduction and utilizing a catalytically active impregnated carbon electrode coated with an electrically conductive permeable ceramic coating for enhanced robustness and stability

SUMMARY OF THE INVENTION

The present invention describes a multilayer reference electrode for the measurement of corrosion potentials. The reference electrode consists essentially of manganese dioxide doped carbon, in equilibrium with air or oxygen, which has been treated to improve exchange current density and decrease peroxide accumulation. This treatment consists of the following steps:

1) pretreating carbon by immersion in a solution of hydrogen peroxide, followed by rinsing and drying to produce pretreated carbon;

2) forming an electrochemically stable catalytic surface on pretreated carbon by impregnating the pretreated carbon with manganese dioxide by submerging the pretreated carbon in a manganese nitrate solution;

3) heating the impregnated carbon to produce carbon doped with betaphase manganese dioxide;

4) wetproofing the manganese dioxide doped carbon with a porous fluorocarbon wetproofing film;

5) coating the manganese dioxide doped carbon with a porous, wettable coating, said porous wetable coating consisting essentially of calcium oxide silicon dioxide and carbon.

OBJECT OF THE INVENTION

It is an object of the present invention to provide a porous carbon and combined ceramic electrode structure with a permanent and electrically stable oxygen-catalyst surface equilibrated with air and capable of producing a reversible redox potential.

It is yet another object of the invention to produce a stable and reproducible reference electrode which is simple to manufacture, rugged to handle and cost effective.

It is yet another object of the invention to provide a reference electrode which can be embedded in concrete for monitoring the corrosion condition of the concrete embedded iron or and steel for research and long-term maintenance of corrosion protection.

PREFERRED EMBODIMENT

In a preferred embodiment, a carbon (graphite) electrode is pretreated by immersion in 30% $H_2O_2$ and then is impregnated with manganese dioxide to produce manganese dioxide doped carbon. In the manganese dioxide treatment of the carbon electrode the pores of the carbon electrode are filled by submerging the carbon block in 1.5 molar manganese nitrate ($Mn(NO_3)_2$) solution; the pressure above the solution is then lowered sufficiently to produce boiling of the manganese nitrate solution, followed by raising the pressure back to atmospheric pressure. After drying overnight at 90 degrees centigrade the electrode is then heated to 200 degrees centigrade for two hours in air to dehydrate the $Mn(NO_3)_2.4H_2O$ and then heated to 400 degrees centigrade for one hour in nitrogen to decompose the $Mn(NO_3)_2$ to $MnO_2$. After this treatment, the carbon is found to contain between 1 and 5 percent by weight of beta-phase manganese dioxide having a so-called beta crystallographic structure. X-ray analysis shows that in such a case the alpha crystallographic manganese dioxide phase is present only in trace amounts in samples heat treated at 300, 350, 450. 500 degrees centigrade in nitrogen. Samples treated at 600 degrees centigrade are found to contain only $Mn_2O_3$ and not $MnO_2$. The preferred temperature range for heat treatment is between 200 and 450 degrees centigrade. In alternative impregnation treatments other metal oxides including platinum oxide, silver oxide, cobalt oxide, molybdenum oxide, tungsten oxide, titanium and columbium oxides can be produced by impregnation of the carbon with soluble salts of these metals, followed by heat treatment to decompose the salt and to produce the metal oxide. After impregnation with manganese dioxide or other metal oxide, the carbon reference electrode is then sprayed with a fluorocarbon polymer or telomer followed by thermal treatment for twenty minutes at 300 to 350 degrees centigrade in nitrogen to produce a wetproofing coating. In the preferred embodiment this wetproofing coating is between 0.0005 and 0.01 inches thick.

Electrical connection to the carbon electrode is made by bonding a metal wire, preferably copper, to the carbon. In the preferred procedure this bonding step is carried out using epoxy resin which has been mixed with conductive carbon powder before hardening. After the electrical connection has been made to the carbon, the carbon assembly is then coated by dipping into a water mixture consisting essentially of a chemical mixture of calcium oxide, silicon dioxide and carbon powder followed by drying and hardening in air at room temperature. The preferred coating mixture has been found to have a ratio (by weight) of essentially 64% calcium oxide, 23% silicon dioxide and the balance carbon powder. However, as much as 74% calcium oxide and as little as 13% silicon dioxide can be used. Alternatively, as much as 33% silicon dioxide and as little as 54% calcium oxide can be used. In all cases in which carbon powder is added to the calcium oxide and silicon dioxide, the carbon content can vary from 0. 15% to 15%.

We claim:

1. A reference electrode for the measurement of corrosion potentials, said reference electrode consisting essentially of beta-phase manganese dioxide-doped carbon as an electrode structure with a permanent and electrically stable oxygen-catalyst surface equilibrated with air and capable of producing a reversible redox potential, said beta-phase manganese dioxide-doped carbon containing between 1 and 5 weight percent of beta-phase manganese , said beta-phase manganese dioxide-doped carbon produced by treating carbon to improve exchange current density when in equilibrium with air or oxygen, decrease peroxide accumulation and produce manganese dioxidedoped carbon, said treatment consisting of the steps of:

1) pretreating said carbon by immersion in a solution of hydrogen peroxide, followed by rinsing and drying to produce pretreated carbon;

2) forming an electrochemically stable catalytic surface on said pretreated carbon by impregnating said pretreated carbon with beta-phase manganese by submerging said pretreated carbon in manganese nitrate solution, 3) heating said impregnated carbon to between 200 degrees centigrade and 400 degrees centigrade to produce carbon doped with with between 1 and 5 weight percent of beta-phase manganese dioxide;

4) wetproofing said beta-phase manganese dioxide-doped carbon with a porous fluorocarbon wetproofing film; whereby said reference electrode for the measurement of corrosion potentials is produced.

2. A reference electrode as disclosed in claim I wherein said fluorocarbon wetproofing coating is between 0.0005 and 0.01 inches thick.

3. A reference electrode as disclosed in claim 1 wherein said calcium oxide of said porous coating is between the limits of 54 and 74 weight percent.

4. A reference electrode as disclosed in claim 1 wherein said silicon dioxide of said porous coating is between the limits of 13 and 33 weight percent.

5. A reference electrode as disclosed in claim 1 wherein said carbon of said porous coating is between the limits of 0.1 5 and 15 weight percent.

6. A reference electrode as disclosed in claim 1 wherein said fluorocarbon wetproofing coating is between 0.0005 and 0.01 inches thick.

7. A reference electrode for the measurement of corrosion potentials. said reference electrode consisting essentially of beta-phase manganese dioxide-doped carbon coated with a porous, wetable coating of calcium oxide, silicon dioxide and carbon to provide a combined ceramic electrode structure with a permanent and electrically stable oxygen-catalyst surface equilibrated with air and capable of producing a reversible redox potential, said beta-phase manganese dioxide-doped carbon containing between 1 and 5 weight percent of beta-phase manganese dioxide doped carbon, said beta-phase manganese dioxide-doped carbon produced by treating carbon to improve exchange current density when in equilibrium with air or oxygen, decrease peroxide accumulation and produce manganese dioxide-doped carbon, said treatment consisting of the steps of:

1) pretreating said carbon by immersion in a solution of hydrogen peroxide, followed by rinsing and drying to produce pretreated carbon;
2) forming an electrochemically stable catalytic surface on said pretreated carbon by impregnating said pretreated carbon with beta-phase manganese by submerging said pretreated carbon in manganese nitrate solution;
3) heating said impregnated carbon to between 200 degrees centigrade and 400 degrees centigrade produce carbon doped with with between 1 and 5 weight percent of beta-phase manganese dioxide;
4) wetproofing said beta-phase manganese dioxide-doped carbon with a porous fluorocarbon wetproofing film;
5) coating said beta-phase manganese dioxide-doped carbon with a porous, wettable coating, said porous wetable coating consisting essentially of calcium oxide, silicon dioxide and carbon, whereby said reference electrode for the measurement of corrosion potentials is produced.

8. A reference electrode for the measurement of corrosion potentials, said reference electrode consisting essentially of beta-phase manganese dioxide-doped carbon as an electrode structure with a permanent and electrically stable oxygen-catalyst surface equilibrated with air and capable of producing a reversible redox potential, said betaphase manganese dioxide-doped carbon containing between 1 and 5 weight percent of beta-phase manganese dioxide doped carbon, said beta-phase manganese dioxide-doped carbon produced by treating carbon to improve exchange current density when in equilibrium with air or oxygen, decrease peroxide accumulation and produce manganese dioxide-doped carbon, said treatment consisting of the steps of:

1) pretreating said carbon by immersion in a solution of hydrogen peroxide, followed by rinsing and drying to produce pretreated carbon;
2) forming an electrochemically stable catalytic surface on said pretreated carbon by impregnating said pretreated carbon with beta-phase manganese by submerging said pretreated carbon in manganese nitrate solution;
3) heating said impregnated carbon to between 200 degrees centigrade and 400 degrees centigrade produce carbon doped with with between 1 and 5 weight percent of beta-phase manganese dioxide;
4) wetproofing said beta-phase manganese dioxide-doped carbon with a porous fluorocarbon wetproofing film;
5) coating said beta-phase manganese dioxide-doped carbon with a porous, wettable coating, said porous wetable coating consisting essentially of calcium oxide, silicon dioxide and carbon, said calcium oxide of said porous coating being between the limits of 54 and 74 weight percent, said silicon dioxide of said porous coating being between the limits of 13 and 33 weight percent, said carbon of said porous coating is between the limits of 0. 15 and 15 weight percent, and said fluorocarbon wetproofing coating being between 0.0005 and 0.01 inches thick, whereby said reference electrode for the measurement of corrosion potentials is produced.

* * * * *